(12) United States Patent
Mann et al.

(10) Patent No.: US 6,718,202 B2
(45) Date of Patent: *Apr. 6, 2004

(54) METHOD OF TREATMENT OF DYSMENORRHEA OR RELIEVING MENSTRUAL CRAMPS

(75) Inventors: Thomas L. Mann, Carlsbad, CA (US); Gregory J. Gruzdowich, Carlsbad, CA (US); Thomas L. Grey, Carlsbad, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/933,326

(22) Filed: Aug. 20, 2001

(65) Prior Publication Data

US 2002/0002388 A1 Jan. 3, 2002

Related U.S. Application Data

(63) Continuation of application No. 09/461,559, filed on Dec. 14, 1999, now Pat. No. 6,282,443.

(51) Int. Cl.$^7$ ................................................ A61N 1/32
(52) U.S. Cl. ........................................ 607/2; 607/46
(58) Field of Search ............................ 607/2, 1, 3, 45, 607/46, 63, 72, 73, 74, 75

(56) References Cited

U.S. PATENT DOCUMENTS

| 4,479,495 A | 10/1984 | Isaacson ................ 128/327 |
| 4,803,986 A | 2/1989 | Dufresne et al. ........ 128/385 |
| 4,981,146 A | 1/1991 | Bertolucci .............. 128/802 |

OTHER PUBLICATIONS

Stux, et al., Basics of Acupuncture, Springer–Verlag, Berline Heidelberg New York (1995).

*Primary Examiner*—Scott M. Getzow
(74) *Attorney, Agent, or Firm*—Michael R. Crabb

(57) ABSTRACT

A method for providing noninvasive electrical stimulation of a single acupuncture site for treatment of menstrual cramps or treating dysmenorrhea.

13 Claims, 2 Drawing Sheets

METHOD OF TREATMENT OF DYSMENORRHEA OR RELIEVING MENSTRUAL CRAMPS

RELATED PATENTS

This application is a continuation of parent application 09/461,559 filed Dec. 14, 1999, now U.S. Pat. No. 6,282,443.

FIELD OF THE INVENTION

The methods and devices described below relate to the fields of treatment of dysmenorrhea or relieving menstrual cramps and noninvasive electrical stimulation of an acupuncture point.

BACKGROUND OF THE INVENTION

Acupuncture has been proposed for the treatment of dysmenorrhea (painful menstruation), specifically menstrual cramps and associated back pain. In *Basics of Acupuncture* (Gabriel Stux and Bruce Pomeranz, Springer-Verlag, Berlin Heidelberg New York, 1995) dysmenorrhea and associated pain are treated via acupuncture applied to Du 20, Ren 3, Ren 6, Ren 4, St.29, LI. 4, Sp.6 (Spleen 6), Sp.10 (Xuehai point, which is the highest point of the m. vastus medialis, proximal to the upper border of the patella), Liv.3, and St.36.

Isaacson, *Acupressure Point Stimulator Device*, U.S. Pat. No. 4,479,495 (Oct. 30, 1984) describes an acupressure device for treating among other things pain of the genitalia and irregular menstruation. The acupressure device applies pressure to specific points on a human body, and for this application the acupoint Spleen Six located near the ankle. The device essentially comprises a stimulator attached to a flexible band and worn for example around the ankle to apply pressure to the spleen six acupoint. The device does not use electrotherapy.

Dufresne et al., Ergonometric Transcutaneous Electrical Nerve Stimulator, U.S. Pat. No. 4,803,986 (Feb. 14, 1989) describes an ergonometric transcutaneous electrical nerve stimulator (TENS) especially designed for menstrual pain, dysmenorrhea and low back pain. It utilizes TENS technology with relatively high power applied locally to the area of pain, masking pain signals of a human body before they reach the brain giving the subject apparent relief from the pain. The ergonometric factors include a housing containing the electrical circuit, the housing being of a generally flatted disk shape with well rounded edges whereby the power switch and current amplitude switches are located on a side edge of the housing. The device has been designed to be attached to the body, for example, the stimulator may be hung from the strap of bras or other undergarments, from a belt at the waist, or "pendant style" from straps fitted around the neck.

Bertolucci, *Nausea Control Device*, U.S. Pat. No. 4,981,146, Jan. 1, 1991, describes a nausea control device in the form of a watch-like housing attachable to the human wrist by an adjustable attachment band. The device uses non-invasive nerve stimulation whereby electricity is passed through two electrodes to stimulate nerves located on the ventral side of the wrist (this anatomical position is sometimes referred to as the palmar side of the wrist. The treatment provided by the device is sometimes referred to as electro-acupuncture which is a form of acupuncture, and the ventral site of application is referred to in the acupuncture art as the P6 point, pericardium 6 point, or master point of the pericardium meridian (sometimes referred to as the vascular meridian). A primary object of the invention is to provide a non-chemical, non-invasive, painless and inexpensive method of alleviating nausea. It is also portable, self-contained and convenient to the patient. Electrical pulse repetition rate of approximately 70 pulses per second and a pulse width of 80 microseconds has been found to provide effective relief of nausea in a patient. Our currently preferred electrical pulse pattern comprises about 350 microsecond pulse width at about 31 pulses per second at power levels of about 10–35 milli-amps peak pulse height. Thus a wide range of pulse patterns may be used in non-invasive nerve stimulation devices.

We have discovered that using noninvasive electrical stimulation of the P6 or Neiguan point of the pericardium meridian relieves menstrual cramps. The effect is obtained without stimulation of other acupuncture points. It takes only a few minutes of stimulation to achieve marked reduction in cramp-like symptoms.

SUMMARY OF THE INVENTION

The method described below employs use of the device described in Bertolucci, Nausea Control Device, U.S. Pat. No. 4,981,146 (Jan. 1, 1991) and similar devices for the relief and alleviation of dysmenorrhea or menstrual cramps.

DETAILED DESCRIPTION OF THE PREFERRED EMBODIMENT

Figure 1:
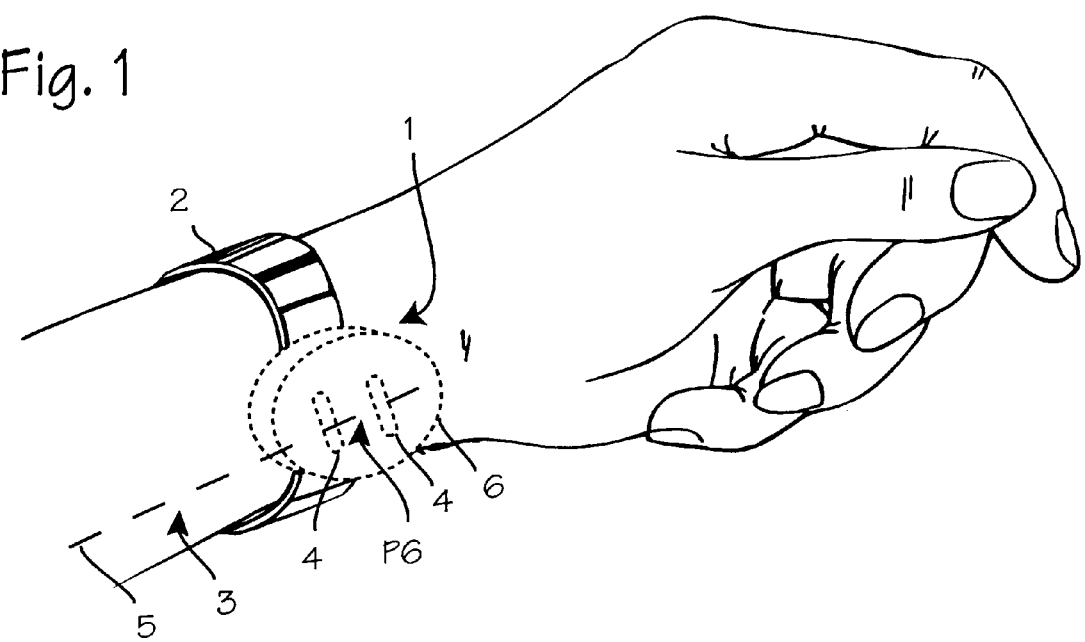
FIG. 1 illustrates placement of an electro-acupuncture device over the P6 acupuncture point on the human wrist.

Use of our ReliefBand® NST™ device for the approved treatment of nausea has revealed that the treatment also relieves menstrual cramps and other menstrual discomfort. Anecdotal reports indicate that the electrostimulation provided to the P6 point on the wrist significantly reduced menstrual cramps. It also alleviated other menstrual discomfort, including dizziness and lower back pain. The ReliefBand® NST™ is a wristwatch like device worn on the wrist and energized to provide electrical stimulation to the wrists. The ReliefBand® NST™ non-invasive nerve stimulation device 1 is secured with strap 2 to the ventral side of the wrist 3 such that the pair of electrodes 4 are disposed over the median nerve 5 (indicated by the phantom line) in contact with the skin in the vicinity of the P6 acupuncture point. The electrodes are on the underside of the housing 6, the required battery and control electronics are housed within the housing, and input mechanisms are located on the outer face of the housing. The electrodes stimulate the median nerve and collateral or associated nerve structures.

Figure 2:
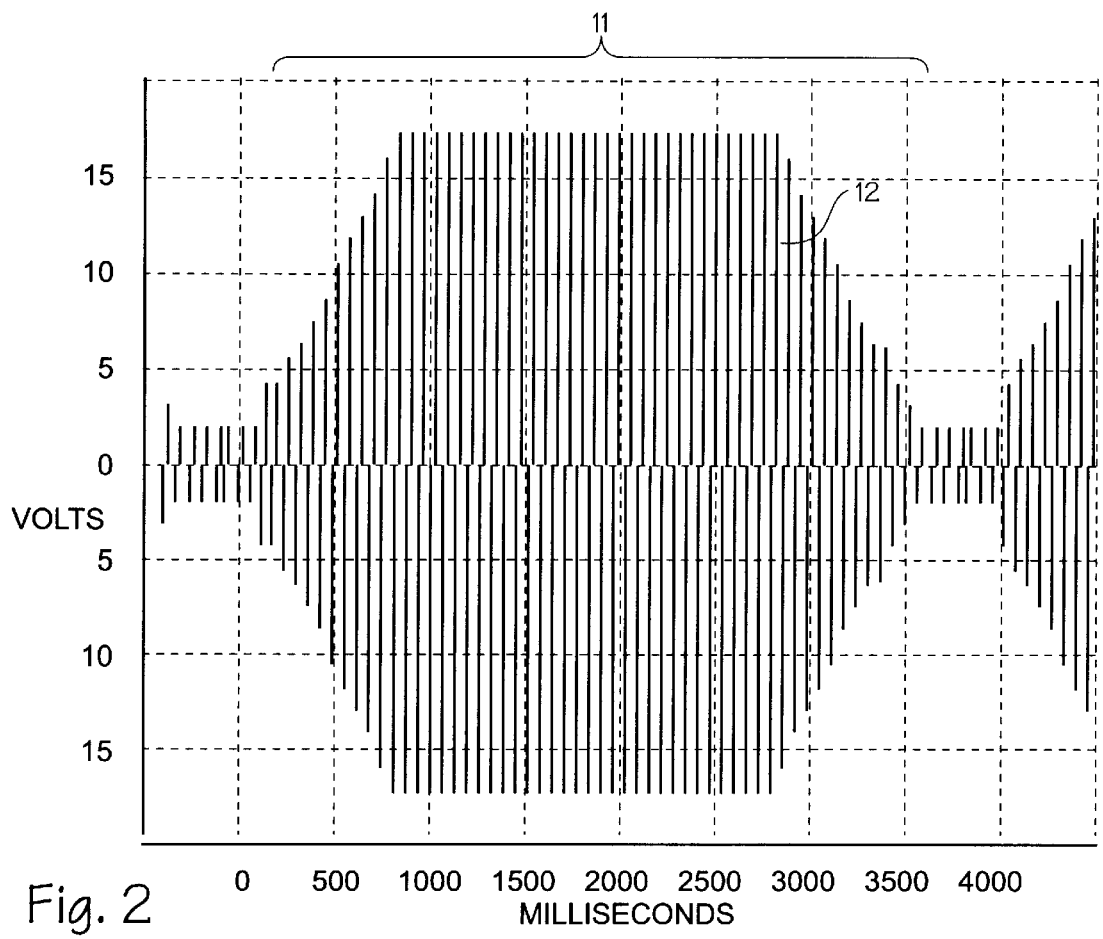
FIG. 2 illustrates a stimulation waveform for stimulating the wrist in accomplishing the treatment.
Figure 3:
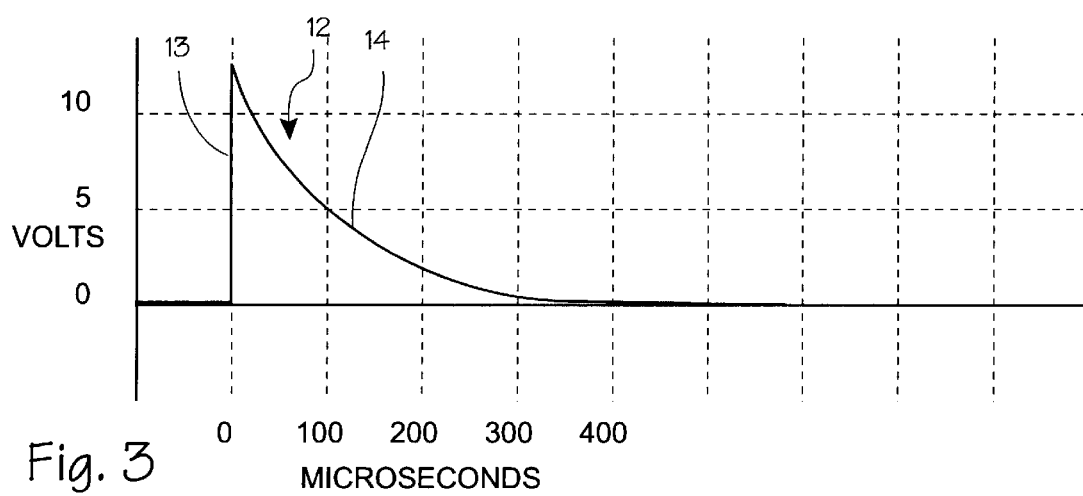
FIG. 3 illustrates an individual pulse of the stimulation waveform.

FIG. 2 shows the preferred waveform. The overall waveform comprises a series of bipolar trapezoidal waveform that make low frequency pulses 11. The waveform is initiated at low power levels of about 1 to 2 volts and ramps up over a period of about 1 second to a maximum level of 17–18 volts, and is maintained for about 2 seconds, and then ramps down over a period of about 1 second to low power levels of about 1 to 2 volts. (The voltage specified is measured across a 500 ohm resistive load as suggested in ANSI/AAMI NS-4 (1986), American National Standard for Transcutaneous Electrical Nerve Stimulators.) The individual pulses 12 are separated by about 32 milliseconds (msec)(measured peak to peak), and last about 350 microseconds (μsec). The individual pulses alternate between negative and positive pulses, and are said to constitute a bipolar waveform. The individual pulses are illustrated in FIG. 3, in which the time scale is enlarged to show the detail. The individual pulse 12 is made of a sharply vertical spike which decays exponentially over a period of about 350 μsec, thus comprising a basically vertical leading edge 13 and an exponentially decaying trailing edge 14 to each individual pulse. The following pulse will be shaped the same, except that it will be of negative voltage. The exponential nature of the individual pulse decay maximizes the high frequency components in the signal. These high frequency components contribute to a lessening of the skin impedance, in particular the capacitive components. This contributes to a higher level of current able to enter the deeper tissues. The power levels may be adjusted up or down to intensify the therapeutic effect of the device or lessen the sensation causes by the device, according to the preferences of individual users. The pulse rate within the waveform may be increased or decreased also.

To use the device to alleviate menstrual cramps, the user merely secures the housing over the inner surface of the wrist and straps it on like a wristwatch. This places the electrodes over the P6 acupuncture point, in electrical contact with the skin overlying the median nerve. The user then turns the device on, adjusts it to a comfortable power level, and allows stimulation to continue for a few minutes, for example 5–10 minute to achieve relief. The device may be applied intermittently, once every hour or so, or continuously. The device provides electrical current and voltage to the electrodes to relieve menstrual pain. The device will eliminate the menstrual cramps entirely, or reduce them to more tolerable levels. While less convenient, the methods may be accomplished with electro-acupuncture needles or electrodes handled individually by an acupuncturist.

While the devices and methods have been described in reference to the environment in which they were developed, they are merely illustrative of the principles of the inventions. Other embodiments and configurations may be devised without departing from the spirit of the inventions and the scope of the appended claims.

We claim:

1. A method of treating dysmenorrhea in a patient comprising the steps of:
   mounting a non-invasive nerve stimulation device onto the ventral side of the wrist;
   generating a stimulation signal;
   delivering the stimulation signal to the ventral side of the wrist to treat dysmenorrhea; and
   leaving acupuncture points located remotely from the wrist untreated by the delivery of a stimulation signal.

2. A method of treating dysmenorrhea in a patient comprising the steps of:
   mounting at least one electrode onto the ventral side of the wrist;
   generating a stimulation signal;
   delivering the stimulation signal to said at least one electrode to stimulate the ventral side of the wrist to treat dysmenorrhea; and
   leaving acupuncture points located remotely from the wrist untreated by the delivery of a stimulation signal.

3. The method of claim 2 wherein said mounting step includes providing a wristwatch-like housing carrying the electrodes, and providing securing means for mounting the housing onto the wrist, with the housing having a circuit means for generating the stimulation signal encased within the housing.

4. The method of claim 2 wherein said delivering step comprises delivering an intermittent stimulation signal.

5. The method of claim 2 wherein said delivering step comprising delivering a continuous stimulation signal.

6. A method of treating dysmenorrhea in a patient by stimulating the median nerve and associated nerve structures in the wrist of the patient with electrical energy without stimulating nerves located remotely from the wrist of the patient.

7. A method of treating dysmenorrhea in a patient, said method comprising the steps of:
   applying an electro-acupuncture device onto the wrist; and
   stimulating the wrist with the electro-acupuncture device to treat dysmenorrhea.

8. A method for treating a patient suffering from dysmenorrhea comprising the steps of:
   engaging an electrode with the P6 acupuncture point on the patient; and
   applying an electrical current to said electrode to treat dysmenorrhea.

9. A method of treating dysmenorrhea in a patient comprising the steps of:
   mounting a non-invasive nerve stimulation device onto the ventral side of the wrist;
   generating a stimulation signal; and
   delivering the stimulation signal to the ventral side of the wrist to treat dysmenorrhea.

10. A method of treating dysmenorrhea in a patient comprising the steps of:
    mounting at least one electrode onto the ventral side of the wrist;
    generating a stimulation signal; and
    delivering the stimulation signal to said at least one electrode to stimulate the ventral side of the wrist to treat dysmenorrhea.

11. The method of claim 10 wherein said mounting step includes providing a wristwatch-like housing carrying the electrodes, and providing securing means for mounting the housing onto the wrist, with the housing having a circuit means for generating the stimulation signal encased within the housing.

12. The method of claim 10 wherein said delivering step comprises delivering an intermittent stimulation signal.

13. The method of claim 10 wherein said delivering step comprises delivering a continuous stimulation signal.

* * * * *